(12) United States Patent
Rist

(10) Patent No.: US 7,246,616 B2
(45) Date of Patent: Jul. 24, 2007

(54) DEVICE FOR INFLUENCING GAS FLOWS

(76) Inventor: Max Rist, Holunderweg 4, 85276 Pfaffenhofen (DE)

( * ) Notice: Subject to any disclaimer, the term of this patent is extended or adjusted under 35 U.S.C. 154(b) by 2 days.

(21) Appl. No.: 10/525,128

(22) PCT Filed: Aug. 14, 2003

(86) PCT No.: PCT/EP03/09041

§ 371 (c)(1),
(2), (4) Date: Aug. 8, 2005

(87) PCT Pub. No.: WO2004/018026

PCT Pub. Date: Mar. 4, 2004

(65) Prior Publication Data

US 2006/0107947 A1    May 25, 2006

(30) Foreign Application Priority Data

Aug. 19, 2002 (DE) .................. 102 38 683

(51) Int. Cl.
*A61M 11/00* (2006.01)
*A61M 15/00* (2006.01)

(52) U.S. Cl. ............... 128/203.12; 128/200.14

(58) Field of Classification Search ......... 128/203.12, 128/203.14, 203.15, 204.11, 204.13, 204.14, 128/200.14
See application file for complete search history.

(56) References Cited

U.S. PATENT DOCUMENTS 4,819,629 A * 4/1989 Jonson ................. 128/203.22
5,320,093 A    6/1994 Raemer
5,687,912 A * 11/1997 Denyer ................. 239/343
5,813,401 A *  9/1998 Radcliff et al. ......... 128/205.24
6,328,030 B1 * 12/2001 Kidwell et al. ......... 128/200.21
6,530,370 B1 *  3/2003 Heinonen .............. 128/200.16
2003/0140919 A1 * 7/2003 Heinonen .............. 128/200.14

FOREIGN PATENT DOCUMENTS

| DE | 43 19 458 A1 | 12/1993 |
| DE | 43 00 880 A1 | 7/1994 |
| DE | 197 26 110 A1 | 1/1999 |
| DE | 199 62 280 A1 | 7/2001 |
| DE | 36 36 669 C2 | 8/2001 |
| DE | 101 18 146 A1 | 10/2002 |
| EP | 0 972 534 A2 | 1/2000 |
| GB | 1190441 A | 5/1970 |
| JP | 05164359 A | 12/1991 |

* cited by examiner

*Primary Examiner*—Justine R. Yu
*Assistant Examiner*—Amadeus Lopez
(74) *Attorney, Agent, or Firm*—McNair Law Firm, P.A.

(57) ABSTRACT

The invention relates to a device for controlling and guiding gas flow in atomizers, in breathing and rebreathing regions of a respiratory appliance. A first embodiment comprises a bypass device; and a said second embodiment comprises a valve which is timed by the respiratory appliance, such that the dead space is not filled with aerosol. Both embodiments provide for an application of aerosol only in the inspiration phase, reduction of the applied medication quantity by reducing the atomization of the dead space, reduction of the side effects of the medications, and sufficient moisturizing of the airways.

2 Claims, 4 Drawing Sheets

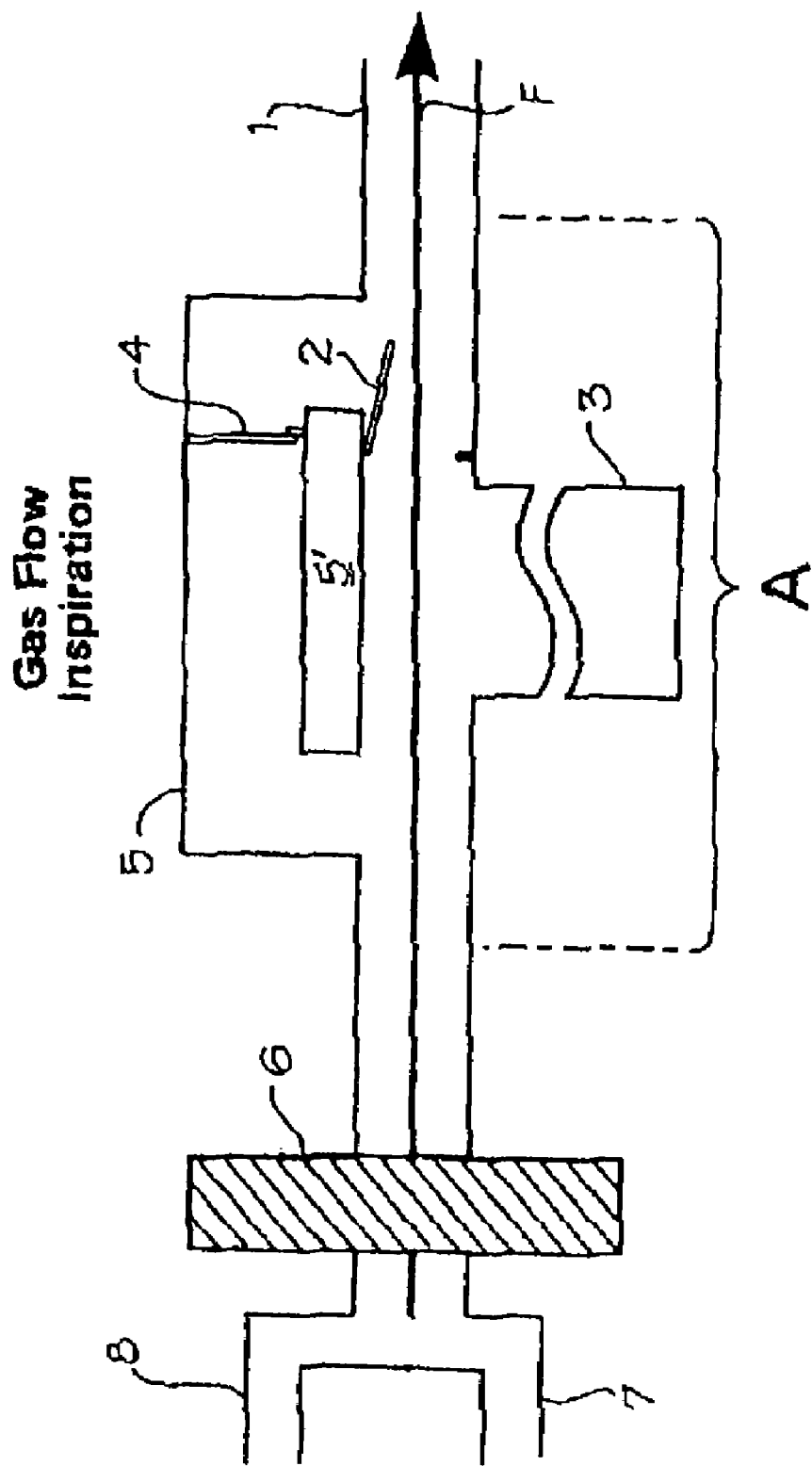

DEVICE FOR INFLUENCING GAS FLOWS

FIELD OF THE INVENTION

This invention relates to respirator appliances and specifically to controlling and guiding the flow of gas within such appliances.

BACKGROUND OF THE INVENTION

With patients suffering from pulmonary diseases, aerosols are often used for therapy. However, special difficulties arise with the utilization of aerosols with patients receiving artificial respiration. Either compressed-air operated nozzle atomizers or atomizers producing aerosols continuously, such as, e.g., ultrasound atomizers or piezoelectric atomizers are used. The nozzle atomizers are normally placed in the common end segment for inspiration and expiration of the artificial respiration hoses, shortly before the tube barrel and are controlled via the artificial respirator, so that they are active only during inspiration. An atomizer is, however, active until the end of inspiration, so that in the overall hose system distal gas enriched with aerosol is present in the atomizer so that the dead-space volume is also provided with aerosol. Thus, it is possible as a rule to place a bacterial filter between the inspiration or expiration legs and the tube barrel, playing also a role in humidifying the respiratory tracts. The heavy humidification of the non-utilized gas column (dead space volume), mostly with large aerosol particles, causes the filter to become filled with liquid and thus loses its antibacterial effect on the one hand, while, on the other hand, the resistance of the filter increases so much that it closes up.

The continuous atomizers such as, e.g., ultrasound atomizers or piezoelectric atomizers produce smaller particles (average size less than 7 µm) that reach the point of utilization more easily, resulting in fewer side effects and lower drug costs. However, these devices can only be placed in the inspiration leg of an artificial respirator since they produce aerosols continuously and would thus convey aerosols to or from the patient during the inspiration as well as during the expiration phase. A filter would, therefore, fill up and lose effectiveness or close up. By omitting a filter, insufficient humidification of the breathing or inhaled air results so that a breathing-air humidifier has to be used which, in addition to costs, also involves a hygienic problem (nosocomial pneumonia). Accordingly, an object of the invention is to create a device in combination with aerosol-producing atomizers that can avoid the foregoing described problems.

SUMMARY OF THE INVENTION

The above object of the invention is attained by means of a device for controlling the direction of gas flow in aerosol producing atomizers in the inspiration and expiration breathing zones of a respirator, with a bypass device which guides the gas as it flows in one direction through the atomizer in order to carry with it aerosol and which guides or diverts the gas past the atomizer via a bypass as it flows in the other direction.

In another aspect the invention is a device to direct the gas flow in atomizers in the inspiration and expiration phases of a respirator by means of a valve that is time-controlled by the respirator and closes before the end of the inspiration function so as not to fill the dead space volume with aerosol.

DESCRIPTION OF THE DRAWINGS

In the drawings appended hereto and made a part of this disclosure by way of illustration and not by way of limitation:

FIG. 1a is a schematic representation of a respiratory appliance having an atomizer showing the arrangement of valves for gas flow in the inspiration phase;

DETAILED DESCRIPTION

My invention makes it possible to place the atomizer (any atomizer can be used) between a filter and tube barrel without a breathing air humidifier at the common end segment of a respirator with the advantage of lower consumption of medicine, fewer side-effects due to applied medicines and longer life of the filter. This is done in the following manner in one embodiment:

The breathing air is conveyed through an atomizer via closing valves (passively or actively controlled as indicated). To make this possible, the valves can be placed at different points in this device. The possibility also exists to use auxiliary devices (e.g., ventilators) in order to optimize the distribution of the aerosol.

In another embodiment, a control cable or hose causes a valve to open in response to the volume of breath, the duration of inspiration, and the pressure of inspiration, so that the dead space is not filled with aerosol. The possibility also exists in this embodiment to use auxiliary devices (e.g., ventilators) to optimize the distribution of the aerosol.

Figure 1B:
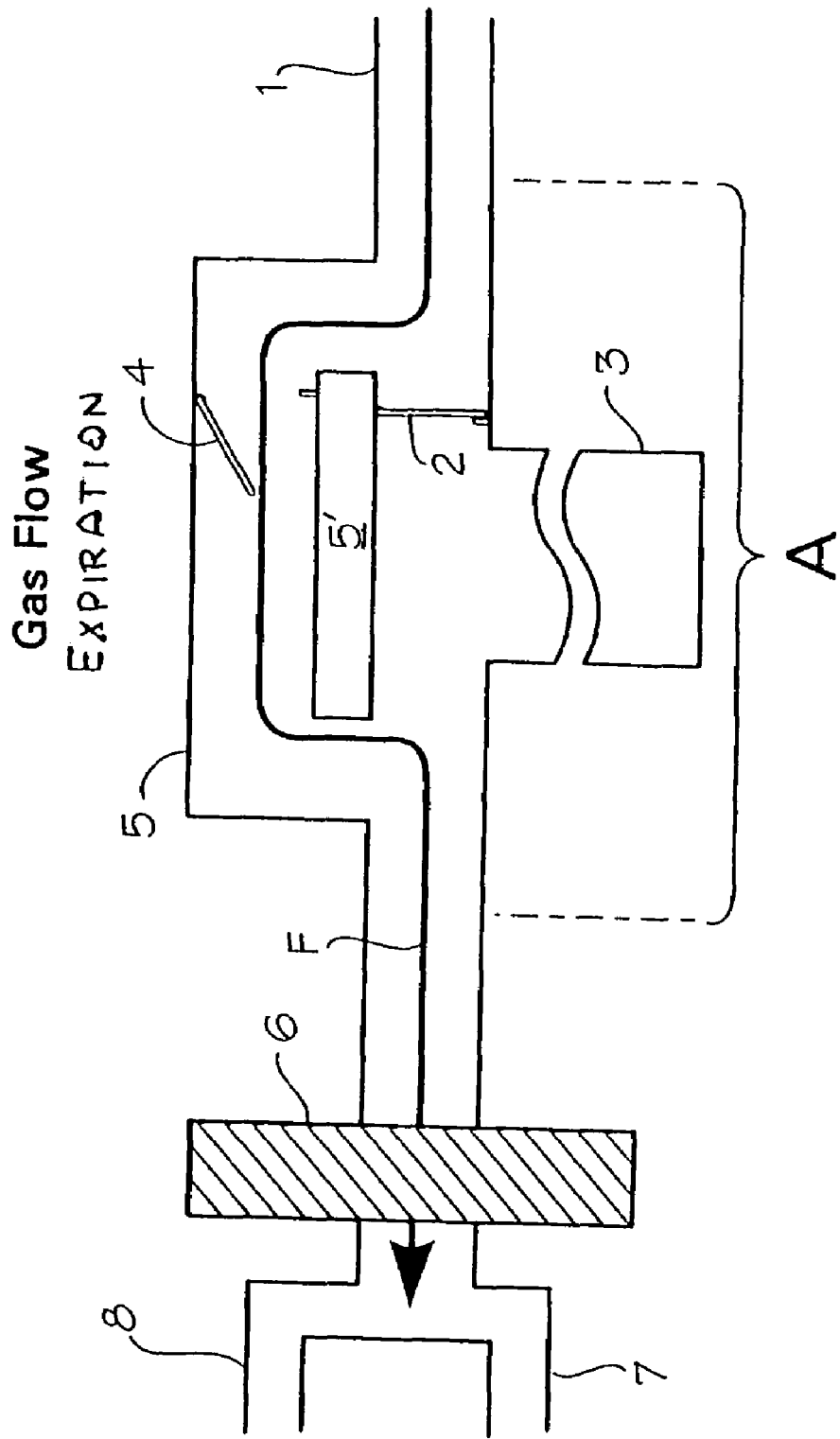
FIG. 1b is the representation of FIG. 1a showing the gas flow in the expiration phase.

The invention is described in greater detail below with reference to the drawings:

FIG. 1a is a schematic diagram of respiratory appliance A or respirator and showing the placement of aerosol producing atomizers 3 (any kind of atomizer can be used) between filter 6 and connection element going to the pipe barrel 7 without breathing-air humidifier at the common end segment (1). This is achieved in that the breathing air is taken through valves (2, 4) (any possible types of valves can be used). During the inspiration phase in FIG. 1a the valve 2 opens and the valve 4 closes (under passive or active control), so that the breathing air (air flow arrow, F) is guided through the atomizer 3. In expiration (FIG. 1b) valve 2 closes and valve 4 opens and the air flow F is guided through bypass 5, 5' avoiding atomizer 3. To make this possible the valves can be placed at different points in this arrangement, e.g., the inspiration valve can be between input and output of the bypass, or the expiration valve can be in the entire bypass. The inspiration leg of the respirator hose is given reference number 7, the expiration leg number 8.

Figure 2A:
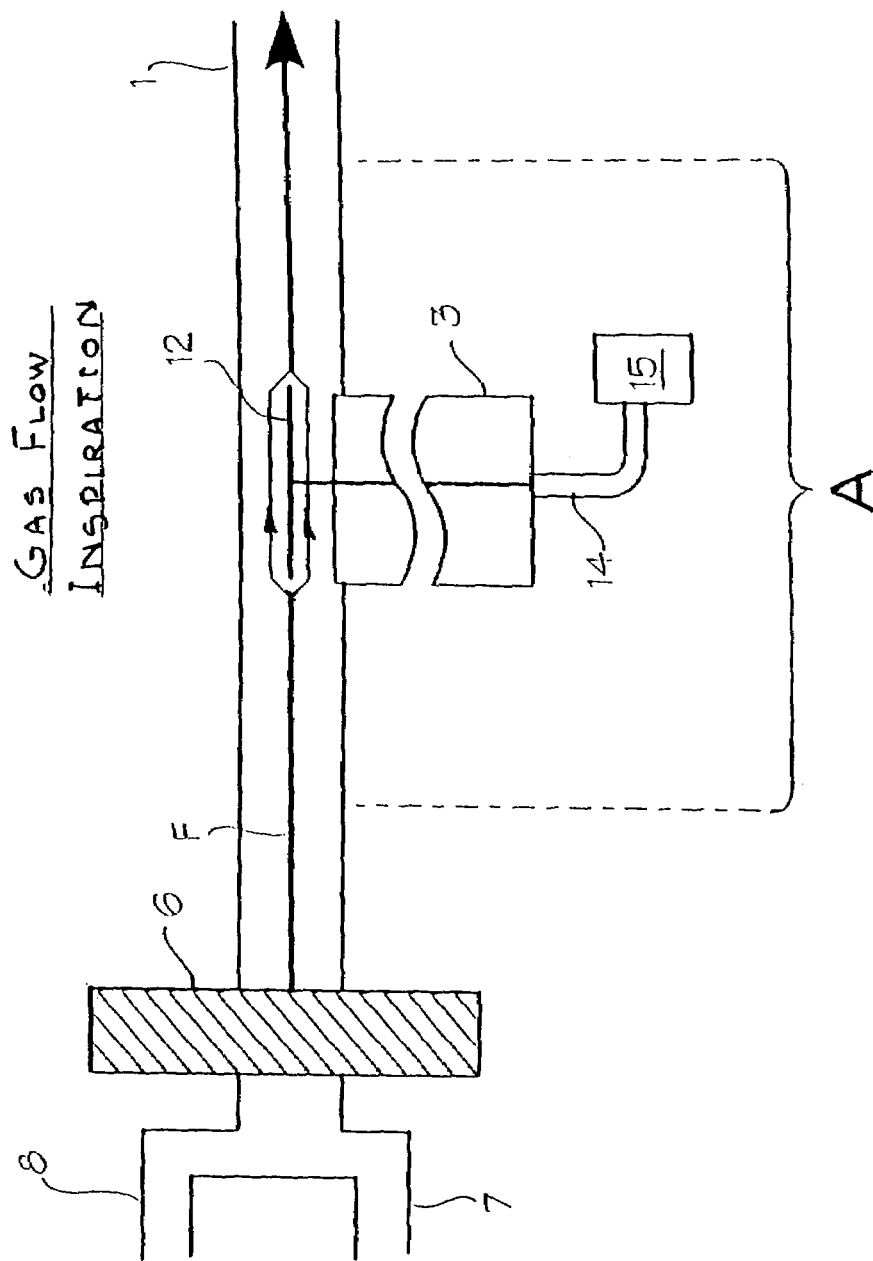
FIG. 2a is a schematic representation similar to FIG. 1a showing control of the flow valve by the respirator during the inspiration phase; and, FIG. 2b shows the representation of FIG. 2a during the expiration phase.
Figure 2B:
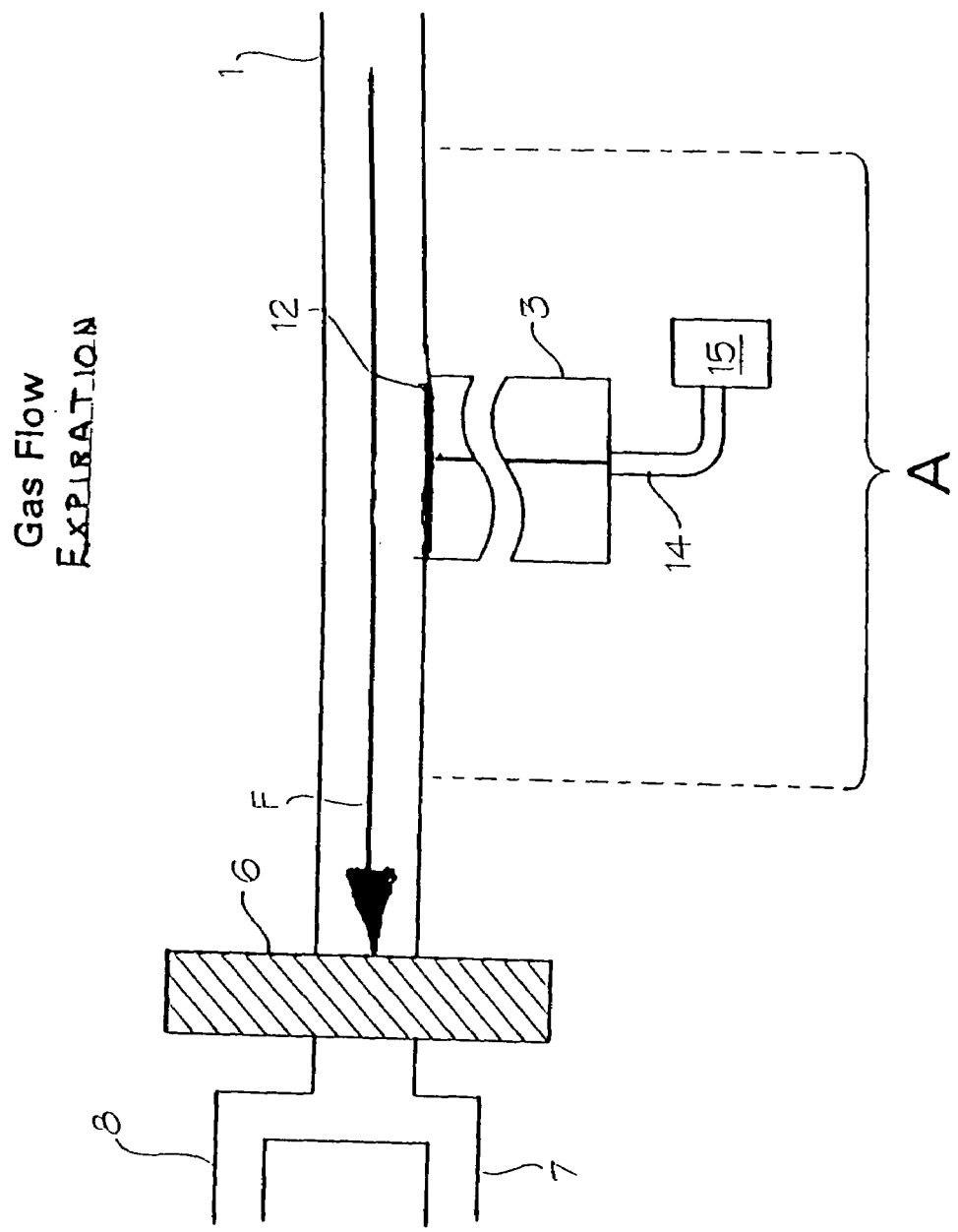

FIGS. 2a, b shows a second embodiment in which any atomizer can be used and which opens valve 12 (any possible type of valve can be used) via a control cable or hose 14 during inspiration for the desired time in response to breath volume, inspiration duration, and inspiration pressure, under control of the respirator 15 (FIG. 2a). At the end of the inspiration phase and in the expiration phase the valve 12 closes so that the dead space volume is not filled with aerosol (FIG. 2b). Number 6 refers to the filter. The inspiration leg of the respirator hose is referenced by number 7 and the expiration leg by number 8.

What is claimed is:

1. A device for controlling the direction of gas or air flow in an in-and-out breathing zone of a respirator which has a patient side end segment, said device comprising:
   a) a single filter for filtering both inspirator and expirator air;
   b) an aerosol producing atomizer positioned in said breathing zone between said filter and said end segment,
   c) by-pass valve means adjacent said atomizer for guiding air through the atomizer as the air flows in one direction to the patient and for by-passing said atomizer as air flows in the other direction.

2. A device for controlling air or gas flow in an aerosol producing atomizer positioned in an in-and-out breathing zone of a respirator having a patient side end segment, said device comprising:
   a) a by-pass valve, said valve being time controlled by the respirator to close and prevent aerosol from filling the dead space volume, and
   b) a single filter for both the inspiration and expiration of air, said atomizer being located between said filter and said patient side end segment so that the patient end segment is close to the atomizer.

* * * * *